United States Patent [19]

Gelb, Jr.

[11] Patent Number: 4,867,975
[45] Date of Patent: Sep. 19, 1989

[54] LIVE ATTENUATED TEMPERATURE-SENSITIVE AVIAN INFECTIOUS BRONCHITIS VIRUS VACCINES AND PREPARATION AND USE THEREOF

[75] Inventor: Jack Gelb, Jr., Landenberg, Pa.

[73] Assignee: University of Delaware, Newark, Del.

[21] Appl. No.: 148,987

[22] Filed: Jan. 27, 1988

[51] Int. Cl.$^4$ ............................................. A61K 39/215
[52] U.S. Cl. ....................................... 424/89; 435/235; 435/237; 435/236; 435/948
[58] Field of Search .................. 424/89; 435/235, 237, 435/948, 236

[56] References Cited

U.S. PATENT DOCUMENTS

| Re. 31,830 | 2/1985 | Apontoweil et al. | 424/89 |
| 3,907,986 | 9/1975 | Zygraich et al. | 424/89 |
| 3,927,208 | 12/1975 | Zygraich et al. | 424/89 |
| 4,053,582 | 10/1977 | Sticki | 424/89 |
| 4,235,876 | 11/1980 | Gits et al. | 424/89 |
| 4,357,320 | 11/1982 | Apontoweil et al. | 424/89 |
| 4,481,188 | 11/1984 | Apontoweil et al. | 424/89 |
| 4,500,638 | 2/1985 | Apontoweil et al. | 424/89 X |
| 4,554,158 | 11/1985 | Russell | 424/89 |
| 4,559,229 | 12/1985 | Page et al. | 424/89 |
| 4,751,079 | 6/1988 | Burger et al. | 424/89 |

OTHER PUBLICATIONS

M. S. Hofstad, *Veterinary Medicine* 51:464–468 (1956).
J. P. Delaplane et al., *Rhode Island Agr. Expt. Station*, Bulletin 284, pp. 4–20 (1941).
H. F. Maassab et al., Proc. Soc. Exptl. Bio. Med. 139:768–773 (1972).
H. F. Maassab, J. Immunol. 102:728–732 (1969).
J. Gelb et al., Avian Diseases 25:655–666 (1981).
J. Gelb et al., Avian Diseases 27:667–678 (1983).
J. Gelb et al., Avian Diseases 27:679–687 (1983).

*Primary Examiner*—Howard E. Schain

[57] ABSTRACT

The cold-adapted (ca) temperature-sensitive (ts) vaccine is prepared by serially passaging a suitably selected virus (e.g. Arkansas-type DPI strain) through a culture medium at a suboptimal replication temperature which is less than about 35° C., e.g. 28° C., and harvesting the live, cold-adapted mutant for formulation into dosage units of, for example, about $10^3$ to about $10^5$ EID$_{50}$/bird. The ca ts mutant is much less able to replicate at 40°–42° C. (internal avian body temperatures) than at the temperature of the bird's upper respiratory tract, which is below 40° C. The vaccine can be administered by any of the usual techniques, including the spray technique. Vaccines of this invention appear to be very effective (immunogenic), but are also safe (non-pathogenic).

13 Claims, No Drawings

LIVE ATTENUATED TEMPERATURE-SENSITIVE AVIAN INFECTIOUS BRONCHITIS VIRUS VACCINES AND PREPARATION AND USE THEREOF

BACKGROUND OF THE INVENTION

1. Field of the Invention

This invention relates to a process for producing a live, attenuated (and cold-adapted) temperature-sensitive vaccine. An aspect of this invention relates to a vaccine for avian infectious bronchitis. Still another aspect of this invention relates to a method for immunizing poultry against avian infectious bronchitis viruses (AIBV). Still another aspect of this invention relates to the live, cold-adapted temperature-sensitive vaccine which is obtained by serial passage of a strain of virus through culture media at suboptimal replication temperatures. A still further aspect of this invention relates to a method for reducing the pathogenicity of an avian infectious bronchitis virus without destroying its immunologic properties. An aspect of this invention specifically relates to Arkansas-type strains of avian infectious bronchitis viruses, whereby these viruses are rendered substantially non-pathogenic without destroying their immunologic properties.

2. Description of the Prior Art

Poultry production accounts for a substantial amount of the total farm income in many areas of the world and can best be described as a large-scale "agribusiness". Like other agribusinesses, its large income-producing ability depends to a great extent upon efficient management. Efficient management has, however, a major disadvantage in that disease risks can be significantly increased and diseases can easily spread through the dense population of birds in a modern poultry farm. Respiratory disease is a particularly severe problem in this particular field of agribusiness and is known to be the cause of substantial business losses. Accordingly, a great deal of scientific expertise and technical skill has been brought to bear on the problem of respiratory disease in poultry, resulting in a variety of strategies for dealing with this problem.

Perhaps the most common strategy involves controlling respiratory disease through vaccination. Currently, there are vaccines available for the viruses of three respiratory diseases, infectious laryngotracheitis, Newcastle disease (ND) and infectious bronchitis (IB). Of these three aspects of avian immunology, AIBV vaccine technology is of particularly great importance. The presently preferred large-scale agribusiness procedure for vaccinating poultry against IB involves the use of live vaccines which are most commonly administered through drinking water, by the eyedrop technique, or by the increasingly popular spray method. As of the present time, the live vaccine appears to provide a far better immunologic response and is the vaccine of choice for broiler chickens and pullets; killed viruses are typically used only as boosters in conjunction with live vaccines and, because of economic constraints; are administered to breeder or layer chickens (e.g. by injection). However, as with any live vaccine, the risk of a pathogenic response may be substantial.

Pathogenicity can be particularly serious in the case of spray vaccination, wherein the poultry are exposed to an aerosol comprising droplets of the vaccine in a suitable liquid carrier. This aerosol technique is used mainly because of its greater savings in labor costs. But despite modification of the live viruses (e.g. attenuation), severe respiratory vaccine reactions in young poultry have been observed in commercial practice.

The success and safety of applying live vaccines by spray depends on several factors, one of which is droplet (particle) size. The smaller the droplet, the greater the potential for severe vaccine reaction. Small droplets may be inhaled directly into lower respiratory tract tissues (lung and airsacs) and may cause disease and mortality particularly when the infection is exacerbated by secondary bacterial agents. Droplet size, however, is difficult or perhaps impossible to control. Realistically, any spray machine is likely to emit droplets of varying size, and environmental factors such as temperature and relative humidity affect the droplet size of a spray.

One approach to the problem of pathogenicity risks in AIBV immunizations has been the development of novel infectious virus strains which are intended to be less virulent but still effective in providing immunity. The following references are believed to be representative of the patent literature relating to modern AIBV technology: U.S. Pat. No. 4,500,638 (Apontoweil et al., February 19, 1985), Re 31,830 (Apontoweil et al., February 12, 1985), 4,481,188 (Apontoweil et al., November 6, 1984) and 4,357,320 (Apontoweil et al., November 2, 1982). Despite recent advances in this field, however, there is still a need for an effective but relatively safer approach to AIBV immunization.

Looking at the entire field of vaccine technology, other approaches to the intertwined goals of safety and effectiveness become apparent, including the technique of attenuation which imparts "temperature sensitivity" to a virus.

Several factors must be considered in attempting to provide a temperature-sensitive (ts) virus. One usual route to temperature sensitivity involves a procedure known as "cold adaptation" (ca) whereby the virus is caused to replicate at a temperature below the optimal temperature of replication, e.g. below 37° C. Unfortunately, not all viruses will reproduce or replicate at suboptimal temperatures. Moreover, even if the virus does replicate at suboptimal temperatures, there is no guarantee that the ca mutant will be sufficiently slow to replicate at internal body temperatures (e.g. about 37° C. in the case of mammals or about 40°–41.5° C. in the case of birds). Finally, even if the ca virus has ts properties, there is no guarantee that the virus will be non-pathogenic at internal body temperatures.

Several workers skilled in the art of developing ts viruses have encountered exactly this problem. Many of the cold-adapted, temperature-sensitive viruses are not entirely desirable as vaccines, because they retain too much pathogenicity at internal body temperatures. Still another problem is that cold adaptation, even at temperatures of 35° C. and less may fail to result in a ts virus. On the other hand, it may be very difficult to obtain any replication at relatively low temperatures, and some viruses cannot replicate at all at temperatures below about 25° or 30° C.

Thus, though ts vaccines for Newcastle disease (ND) have been reported, as in U.S. Pat. No. 4,235,876 to Gits et al. (November 25, 1980), the use of these vaccines has sometimes resulted in undesirable levels of pathogenic response.

According to the patent and scientific literature, there has been some success in developing ts influenza viruses which are avirulent. See Maassab et al., Proc.

Soc. Exptl. Bio. Med. 139:768–773 (1972), Maassab, J. Immunology, 102:728–732 (1969), and references cited in these articles. There is also a body of patent and scientific literature regarding ca live Sendai viruses and various bovine viruses. See, for example, U.S. Pat. No. 3,907,986 (Zygraich et al., Sept. 23, 1975), U.S. Pat. No. 3,927,208 (Zygraich et al., Dec. 16, 1975), and U.S. Pat. No. 4,554,158 (Russell, Nov. 19, 1985).

SUMMARY OF THE INVENTION

Although any AIBV vaccine can be attenuated to some degree by serial passage through suitable cultures at incubation temperatures in the range of 35°–39° C., this procedure does not produce cold-adapted (ca) or temperature-sensitive (ts) live vaccines. In accordance with the present invention, AIBV ts mutant strains are produced by selection through serial passage of AIBV at suboptimal replication temperatures below 35° C., e.g. 28° C. Culture media suitable for suboptimal replication include embryonating chicken eggs, cell cultures, etc. Resulting ca virus can be shown to be ts by determining its ability to multiply at a permissive temperature such as 37° C. but not at a non-permissive temperature such as 41° C.

The method for producing a live, ca ts AIBV vaccine in accordance with this invention comprises:

a. serially passaging a strain of AIBV about 10 to about 100 times (preferably 10–50 times) through a suitable medium at a suboptimal replication temperature which is less than about 35° C., thereby obtaining a live, ca mutant of the parent AIBV strain;

b. harvesting the live, cold-adapted mutant; and c. combining the isolated, live ca mutant with a therapeutically effective amount of a therapeutically effective extender.

The preferred parent AIBV described herein is the Arkansas-type DPI strain (Ark DPI), see Avian Diseases, 25:655–666 (1981), and 27:667–687 (1983), which is commercially available is the form of the AIBV vaccine "BROILERBRON-99" (trade designation of Sterwin Laboratories, Inc., Millsboro, Delaware, U.S.A.). In accordance with this method, ca ts mutants of surprisingly low pathogenicity have been obtained. The preferred mutant has been developed from the Arkansas-type DPI strain and is identified by the microorganism accession number ATCC VR 2200. Suitable dosage units for the live, ca ts AIBV have been developed. This ts vaccine is suitable for use in the common methods of administration to poultry, including the eyedrop and drinking water routes as well as the spray (aerosol) technique. As noted previously, the spray technique seems to be the most efficient and effective, and this is particularly true when vaccinating broiler and pullet chickens.

DETAILED DESCRIPTION

A variety of AIBV strains are readily available from commercial and government sources. A preferred government source is the National Animal Disease Center in Ames, Iowa. Studies in the literature discuss reference AIBV strains such as the Massachusetts, Connecticut, JMK, Gray, Holte, Arkansas 99, Florida, Maine 209, Iowa 97, Iowa 69, and SE 17. Of these, strains of the Massachusetts type are among the preferred ones for controlling IB. Various Arkansas-type strains (including Ark DPI) have become important in recent years. As is known in the art combinations of strains of AIBV can be used as well as combinations of AIBV with other types of vaccines (e.g. ND vaccine).

Although various strains of AIBV can be used in the context of this invention, for convenience of description the disclosure which follows will be directed primarily to the Arkansas-type DPI strain which, without modification, is neither cold-adapted nor temperature-sensitive. However, both of these properties have been observed in the mutants obtained in accordance with this invention. The performance of the mutants has been evaluated both in vitro and in vivo. The in vitro tests show replication at temperatures below 41° C., e.g. The temperatures found in the respiratory system of birds (which are cooler than the internal body temperature). The replication of these mutants at 41° C. is dramatically impaired—a clear indication of ts behavior.

In vivo tests were conducted in bird populations, and a low incidence of respiratory disease from the vaccine was observed. These data, coupled with the in vitro data, are considered to provide strong proof of low pathogenicity as well as ts behavior.

Vaccines prepared in accordance with this invention can be combined with other conventional vaccines, using techniques which are known per se. It is conventional in the poultry vaccine art to combine various vaccines, provided there is no interference between them. In the case of spray treatment of chickens, the conventional approach is to combine live vaccines only. When vaccination is done by injection, killed vaccines are generally utilized as boosters after the administration of live vaccines.

Before the cold-adaptation process is begun, it is greatly preferred to employ cloning techniques in order to obtain a relatively pure strain of AIBV.

The parent, non-ca strain is preferably passaged 10 to 50 times and then adapted to chicken kidney cell (CKC) cultures incubated at 37° C. The parental virus thus obtained can be cloned by isolation of plaques formed on CKC incubated at 37° C. The resultant clones are the parental cloned virus from which the ca mutants are obtained. Alternatively, cloning can be carried out by the limit dilution method.

These cloned viruses have no ts properties and are strongly pathogenic. The pathogenic strain is then ready for serial passage through a suitable medium, embryonated chicken egg passage being normally preferred.

Nine-to-eleven day old chicken embryos can be pre-incubated at 28° C. for 24 hours prior to inoculation of the pathogenic parental cloned virus via the chorioallantoic sac route. Allantoic fluids are harvested at about 96–120 hours post-inoculation. After 10 passages at a temperature above 25° C. but less than 30° C. (e.g. 28° C.), viruses can be screened for evidence of ts character by growth in embryos at permissive (e.g. 37° C.) and non-permissive (e,g, 41° C.) temperatures. As a control, parental cloned virus derived from the same number of embryo passages at the optimal growth temperature (37° C.) are compared for ts behavior. Studies have also been carried out with regard to antigenicity and genetic stability. It is generally expected in this art that the lack of genetic stability of ts mutants is a serious problem. For example, Newcastle disease virus ts mutants have been found to revert to virulence at internal body temperatures during serial passage in chickens. In other areas of the vaccine art, it has been necessary to resort to gene-splicing in order to lower multiplication rates at internal body temperatures. Mutagenic chemicals have also been used, and a variety of cold-adaptation temperatures have been selected in the prior art. In the context of this invention, however, the best results seem to be obtained without chemical mutagens or gene-splicing, provided that the cold adaptation temperature is properly selected. The presently preferred cold-adaptation temperature is 28° C.

Up to 100 passages of the Arkansas-type DPI strain of IB virus have been carried out at 37° C. However, passage 100 virus produces a less than satisfactory immune response. Accordingly, it is preferred for the ts AIBV also that the number of passages for cold adaptation be less than 100, e.g. about 50.

It has been found that the ts AIBV vaccines of this invention are surprisingly safe and effective despite some tendencies to revert and lose ts character. A ts mutant can be a conditional lethal mutant; that is, it is defective in its ability to multiply at high (non-permissive) temperatures and thus behaves as a highly attenuated virus at these temperatures. This behavior makes it possible to take advantage of temperature gradients that exist in the bodies of birds. The temperatures in the upper respiratory tract tissues (nasal sinuses and trachea) are lowered by evaporative cooling, while internal body temperatures rise from 40.2° C. to 41.0° C., between hatching and 6 days of age, particularly in the case of chickens. After the first week of life, the internal body temperature of a chicken remain relatively constant (41.0–41.5° .). By the time the ts AIBV vaccines of this invention lose some of their ts character, the immune system of the chicken has become surprisingly effective in resisting IB.

The Arkansas-type DPI (Ark-DPI) strain of IB virus is a typical coronavirus. The coronaviruses are a family of RNA viruses of similar size and configuration. IBV is a member of the coronavirus family that causes infectious bronchitis, including lethal forms of this disease caused by complicating bacterial infections with *Escherichia coli* or *Mycoplasma sp*. The Arkansas-type DPI strain is one of many different strains that can cause IB.

Serial passage of Ark DPI is described in Gelb et al., Avian Diseases, 27:679–687 (1983). Titers of AIBV are measured in terms of 50% embryoinfectious dose ($EID_{50}$).

Pathogenicity of AIBV can be studied in young chickens inoculated via the intratreachal route with at least $10^5$ $EID_{50}$ of virus per bird. Clinical signs such as coughing, rales, depression, and death can indicate IB, and tissues can be sampled for virus at various times after inoculation. The tissue samples can be evaluated for gross or microscopic lesions.

Immunogenicity of ca mutants is determined by inoculating susceptible chickens with AIBV vaccine and, 28 days later, infecting the chickens with $10^5$ $EID_{50}$ per chicken of challenge virus. Four or five days after challenge, tracheal swabs are obtained from each chicken. The swabs are placed in a tube containing sterile broth and antibiotics, and stored at below −40° C. The broth is evaluated for challenge IBV by embryonated egg inoculation. The failure to reisolate challenge IBV is indicative of immunity.

Following these procedures, low pathogenicity are good immunogenicity of the ts mutants of this invention have been demonstrated.

Although the vaccines of this invention are specific for IB, the sharply reduced stress from IB under commercial conditions has contributed to the general health of the birds, resulting in less stunted growth, less complications from coliform bacteria and less overall mortality.

Any of the commercially practical modes of administration can be used with vaccines of this invention, including the eyedrop, drinking water, and spray routes. In the spray (aerosol) route of administration, for example, the vaccine is combined with a suitable liquid carrier such as water so that it can be conveniently introduced into a conventional spraying machine.

The ca ts AIBV vaccine of this invention can be packaged with or without diluent in 1000-dose vials, 10,000-dose vials, etc. The dosage per chicken is, preferably greater than $10^2$ $EID_{50}$ and less than about $10^6$ $EID_{50}$. Even $10^5$ $EID_{50}$/chicken may be economically undesirable in some cases, and doses as low as $10^3$ $EID_{50}$ per chicken appear to be fully effective, hence larger doses are typically not needed.

In the Examples which follow, egg passage 50 parent strain was either (a) cold-adapted at 28° C. for 10 passages or 20 passages or (b) passaged 10 or 20 times at 37° C. (for comparison purposes). For the in vitro experiments, titrations were carried out at 37° C. and 41° C. to determine temperature-sensitivity. Egg passage 50 Arkansas-type DPI strain of AIBV was not ts when passaged 10 times at 37° C., but the same egg passage 50 was ts when passaged 10 times at 28° C. The novel ca/ts AIBV was found to be safer than the current conventional vaccine in chickens. This represents a major improvement over the current conventional vaccine.

These non-limiting Examples illustrate the principle and practice of this invention.

EXAMPLE 1: DEMONSTRATION OF TEMPERATURE-SENSITIVITY

The effect of temperature on Arkansas-type DPI strain IB virus multiplication in 11-day-old specific-pathogen-free chicken embryos inoculated via allantoic cavity was determined for egg passage 10 and egg passage 50 parent strain at the two adaptation temperatures, 37° and 28° C. The results are reported in Table 1.

TABLE 1

Effect of temperature on Arkansas-type DPI strain infectious bronchitis virus multiplication in 11-day-old specific-pathogen-free chicken embryos inoculated via the allantoic cavity.

| Virus | Adaptation Temp. (°C.) | Adaptation Temp. Passage Number | Titration Temp. 37° C. | Titration Temp. 41° C. |
|---|---|---|---|---|
| Egg Passage 10 | 37 | 10 | 7.4[4] | 7.9 |
| Egg Passage 10 | 28 | 10 | 8.2 | 5.1 |
| Egg Passage 50 | 37 | 10 | 8.0 | 7.2 |
| Egg Passage 50 | 28 | 10 | 7.2 | ≦1.0 |

[4]Embryo infectious dose$_{50}$ per ml (log 10).

EXAMPLE 2

The effect of temperature on Arkansas-type DPI strain IB virus multiplication was investigated in primary chicken kidney cell cultures. Again, egg passage 10 and egg passage 50 parent strain was adapted at 37° and 28° C. The results are reported in Table 2.

TABLE 2

Effect of temperature on Arkansas-type DPI strain infectious bronchitis virus multiplication in primary chicken kidney cell cultures.

Adaptation

TABLE 3

Virus multiplication of cold-adapted and non-cold-adapted Arkansas-type DPI strain infectious bronchitis virus in chicken embryos incubated at 28° C. and 37° C.

| Virus | Adaptation Temperature | Incubation Temperature | Hours Postinoculation | | | | |
|---|---|---|---|---|---|---|---|
| | | | 6 | 12 | 24 | 48 | 72 |
| Egg Passage 50 | 37 | 37 | 3.3[A] | 6.0 | 8.5 | 6.8 | 6.8 |
| | 37 | 28 | <1.0 | 1.3 | 1.3 | 3.8 | 4.5 |
| Egg Passage 50 | 28 | 37 | <1.0 | <1.0 | 4.8 | 5.5 | 4.5 |
| | 28 | 28 | <1.0 | 1.0 | 3.0 | 4.8 | 5.5 |

[A]Embryo infectious dose$_{50}$ per ml (log$_{10}$).

TABLE 4

Pathogenicity of cold-adapted and non-cold-adapted Arkansas-type DPI strain infectious bronchitis virus for 7-day-old broiler chickens[A] inoculated via the intratracheal route (Trial 1).

| Virus | Adaption Temperature (°C.) | Percent of Chicks With Respiratory Disease (Days Post Inoculation) | | | | | | | | | | % Airsacculitis[B] | % Mortality |
|---|---|---|---|---|---|---|---|---|---|---|---|---|---|
| | | 1 | 2 | 3 | 4 | 5 | 6 | 7 | 8 | 9 | 10 | | |
| Egg Passage 10 | 37 | 0 | 20 | 60 | 80 | 70 | 90 | 50 | 70 | 80 | 10 | 0 | 0 |
| Egg Passage 10 | 28 | 0 | 20 | 0 | 20 | 10 | 0 | 10 | 20 | 10 | 0 | 0 | 0 |
| Egg Passage 50 | 37 | 0 | 30 | 50 | 60 | 70 | 60 | 80 | 80 | 20 | 30 | 0 | 0 |
| Egg Passage 50 | 28 | 0 | 0 | 0 | 0 | 0 | 20 | 0 | 0 | 0 | 10 | 0 | 0 |

[A]Ten chickens per treatment.
[B]Chickens examined for airsaculitis at 14 days post inoculation.

TABLE 5

Pathogenicity of cold-adapted and non-cold-adapted Arkansas-type DPI strain infectious bronchitis virus for 3-day-old broiler chickens[A] inoculated via the intratracheal route.

| Virus | Adaptation Temperature (°C.) | Percent of Chicks With Respiratory Disease (Days Post Inoculation) | | | | | | | | | | % Airsacculitis[B] | % Mortality |
|---|---|---|---|---|---|---|---|---|---|---|---|---|---|
| | | 1 | 2 | 3 | 4 | 5 | 6 | 7 | 8 | 9 | 10 | | |
| Egg Passage 50 | 37 | 0 | 18 | 60 | 48 | 30 | 76 | 56 | 64 | 47 | 44 | 10 | 4 |
| Egg Passage 50 | 28 | 0 | 4 | 16 | 28 | 6 | 40 | 30 | 42 | 30 | 38 | 2 | 0 |

[A]Fifty chickens per treatment.
[B]Chickens examined for airsacculitis at 14 days postinoculation.

| Virus | Adaptation Temp. (°C.) | Temp. Passage Number | Titration Temp. | |
|---|---|---|---|---|
| | | | 37° C. | 41° C. |
| Egg Passage 10 | 37 | 10 | 5.9[A] | 4.1 |
| Egg Passage 10 | 28 | 10 | 5.7 | ≦1.0 |
| Egg Passage 50 | 37 | 10 | ≧7.0 | ≧7.0 |
| Egg Passage 50 | 28 | 10 | 6.3 | ≦1.0 |

[A]Plaque forming units per ml (log 10).

EXAMPLE 3: DEMONSTRATION OF COLD-ADAPTED PROPERTIES

Virus multiplication of egg passage 50 ca and non-ca Ark DPI IBV was determined post-inoculation at 37° C. and 28° C.; see Table 3.

EXAMPLE 4: IN VIVO TESTING

The pathogenicity of ca and non-ca Arkansas-type DPI strain IB virus was tested in 7 day-old broiler chickens (Table 4) and in 3 day-old broiler chickens (Table 5) both inoculated via the intratracheal route. The results indicated a substantial pathogenic response when the adaptation temperature was 37° C., but a very low pathogenic response when the adaptation temperature was 28° C.

Vaccinated chickens were challenged with $10^5$ EID$_{50}$ dose per chicken of virulent homologous virus at 28 days post vaccination to determine the immune response. A chicken was considered to be protected (immunized) if the challenge virus could not be reisolated from the chicken. The entire vaccination dose range of $10^3$ to $10^5$ EID$_{50}$ per chicken was found to be effective in providing 100% protection (Table 6).

TABLE 6

Results of challenge of immunity of chickens vaccinated intraocularly at 1-day-old with different doses of cold-adapted Arkansas-type DPI strain infectious bronchitis virus and challenged with $10^5$ embryo infectious dose$_{50}$ per chicken of virulent homologous virus at 28 days post vaccination.

| Virus | Adaptation Temperature | Vaccination Dose Per Chicken | Challenge of Immunity |
|---|---|---|---|
| Egg Passage 50 | 28 C | $10^{3A}$ | 0/15[B] (100%)[C] |
| Egg Passage 50 | 28 C | $10^4$ | 0/15 (100%) |
| Egg Passage 50 | 28 C | $10^5$ | 0/15 (100%) |
| None | — | — | 15/15 (0%) |

[A]Embryo infectious dose$_{50}$ of vaccine.
[B]Number of chickens from which virulent challenge virus was reisolated at 5 days after challenge/Total.
[C]Percent protection = percentage of chickens from which the virulent challenge virus was not reisolated.

What is claimed is:

1. The process for producing a live, cold-adapted temperature-sensitive avian infectious bronchitis virus vaccine which comprises:
   a. serially passaging a strain of an avian infectious bronchitis virus about 10 to about 100 times through a culture medium at a suboptimal replication temperature which is greater than 25° C. and up to about 30° C., thereby obtaining a live, cold-adapted mutant of the parent avian infectious bronchitis virus strain;

b. harvesting the live, cold-adapted mutant; and c. combining the isolated, live cold-adapted temperature-sensitive mutant with a pharmaceutically acceptable amount of a pharmaceutically acceptable diluent.

2. A method according to claim 1, wherein the parent avian infectious bronchitis virus is the Arkansas-type DPI strain.

3. A process according to claim 1, wherein the isolated, live, cold-adapted temperature-sensitive mutant is less able to replicate at 41° C. as compared to its ability to replicate at 37° C.

4. A process according to claim 1, wherein the suboptimal replication temperature is about 28° C.

5. A live, cold-adapted, temperature-sensitive avian infectious bronchitis vaccine comprising a mutant of a Massachussetts type strain of avian infectious bronchitis virus, prepared by the process of claim 1.

6. A live, cold-adapted, temperature-sensitive avian infectious bronchitis vaccine comprising a mutant of Arkansas-type DPI strain avian infectious bronchitis virus, prepared by the process of claim 1.

7. A vaccine combination comprising a live, cold-adapted temperature-sensitive avian infectious bronchitis vaccine prepared according to claim 1.

8. A cold-adapted, temperature-sensitive mutant of the Arkansas-type DPI strain of avian infectious bronchitis virus, developed from said Arkansas-type DPI strain by cold adaptation at a temperature of about 28° C., identified by the microorganism accession number ATCC VR 2200, and characterized by a greater ability to replicate at 37° C. than at 41° C.

9. A dosage unit of live, cold-adapted temperature-sensitive avian infectious bronchitis vaccine prepared according to the method of claim 1, for administration to chickens, consisting essentially of more than $10^2$ $EID_{50}$ but less than about $10^6$ $EID_{50}$ per chicken of said vaccine.

10. A dosage unit according to claim 9, wherein said dosage unit, per chicken, is about $10^3$ to about $10^5$ $EID_{50}$ and is blended with a pharmaceutically acceptable diluent for the vaccine.

11. A method of immunizing poultry against avian infectious bronchitis viruses, comprising the step of:

administering to the poultry, after hatching, a vaccine prepared in accordance with the method of claim 1.

12. A method of immunization according to claim 11, wherein the vaccine is administered by exposing the poultry to an aerosol comprising droplets of liquid containing said vaccine.

13. A process according to claim 1, wherein, in said step a, the avian infectious bronchitis virus is serially passaged through the culture medium at least about 50 but less than 100 times.

* * * * *

UNITED STATES PATENT AND TRADEMARK OFFICE
CERTIFICATE OF CORRECTION

PATENT NO. : 4,867,975
DATED : September 19, 1989
INVENTOR(S) : Jack Gelb, Jr.

It is certified that error appears in the above-identified patent and that said Letters Patent is hereby corrected as shown below:

In column 5:

line 43, "embryoinfectious" should read --embryo infectious--;

line 62, "are" should read --and--.

In column 7, Table 2 is split in half, second half of table appears under Table 5.

Signed and Sealed this

Eleventh Day of September, 1990

Attest:

HARRY F. MANBECK, JR.

*Attesting Officer*      *Commissioner of Patents and Trademarks*